United States Patent
Skinner

(10) Patent No.: US 11,865,040 B2
(45) Date of Patent: Jan. 9, 2024

(54) VITRECTOMY CUTTER

(71) Applicant: Bausch + Lomb Ireland Limited, Dublin (IE)

(72) Inventor: Allen Skinner, Chesterfield, MO (US)

(73) Assignee: Bausch + Lomb Ireland Limited, Dublin (IE)

( * ) Notice: Subject to any disclaimer, the term of this patent is extended or adjusted under 35 U.S.C. 154(b) by 121 days.

(21) Appl. No.: 17/316,117

(22) Filed: May 10, 2021

(65) Prior Publication Data
US 2022/0354693 A1    Nov. 10, 2022

(51) Int. Cl.
*A61F 9/007*    (2006.01)

(52) U.S. Cl.
CPC ................... *A61F 9/00736* (2013.01)

(58) Field of Classification Search
CPC ............. A61F 9/00736; A61F 9/00754; A61B 17/32002; A61B 2017/320028; A61B 17/320068

See application file for complete search history.

(56) References Cited

U.S. PATENT DOCUMENTS

| | | | | |
|---|---|---|---|---|
| 5,020,535 A * | 6/1991 | Parker | ..................... | A61M 1/72 606/174 |
| 8,540,743 B2 * | 9/2013 | Auld | ................... | A61F 9/00763 606/171 |
| 9,924,963 B2 * | 3/2018 | McDonell | ........... | A61F 9/00763 |
| 2011/0144675 A1 * | 6/2011 | Gao | .................... | A61F 9/00736 606/167 |

* cited by examiner

*Primary Examiner* — Timothy J Neal
*Assistant Examiner* — Moira E Hayes
(74) *Attorney, Agent, or Firm* — Harness, Dickey & Pierce, P.L.C.

(57) ABSTRACT

A vitrectomy system includes a surgical cutting apparatus and a processor. The system includes a cutting assembly with an outer cutter and an inner cutter. The cutting assembly includes a housing containing a drive chamber, a spring chamber, at least a first diaphragm. The first diaphragm is adhered to the inner cutter and positioned between the drive chamber and the spring chamber. The system also includes a drive chamber valve to supply compressed air to the drive chamber and a spring chamber valve to adjust air pressure within the spring chamber. The processor is configured to pulse the drive chamber valve based on a desired cut rate to translate the inner cutter and adjust the air pressure within the spring chamber based on the desired cut rate to adjust the stiffness of the spring chamber.

8 Claims, 2 Drawing Sheets

VITRECTOMY CUTTER

FIELD

The present disclosure relates to a surgical instruments for use in ophthalmic surgery, and in particular, to a reciprocating guillotine-type vitrectomy cutter for excising the vitreous and other tissue from an eye.

BACKGROUND

This section provides background information related to the present disclosure which is not necessarily prior art.

Known reciprocating vitrectomy cutters have fixed coiled compression springs for returning or retracting an inner cutting member after it has extended to cut tissue via pneumatic or mechanical means. The spring, which is typically a linear device, must be sized to work over a large cut rate window that could vary from a single cut to many thousands of cuts per minute. Hence, the single, fixed spring constant or stiffness of the spring must accommodate a need to return the inner cutting member to a start position very fast for high cut-rates but not require an unacceptably high drive force to extend the inner cutting member to affect a cut of tissue. A stiffer compressed spring will return the inner cutting member faster than a less stiff spring at an equal resistance against the spring. For pneumatically driven vitrectomy cutters this presents a problem because building up a sufficient drive pressure to extend the inner cutting member and venting that pressure sufficiently to allow the spring to retract the inner cutting member may take excessive time at higher cut rates. Therefore, there is a need for a spring whose stiffness can be varied during use, to optimize the cutting efficiency across the required cut-rate window.

DRAWINGS

The drawings described herein are for illustrative purposes only of selected embodiments and not all possible implementations, and are not intended to limit the scope of the present disclosure.

Corresponding reference numerals indicate corresponding parts or features throughout the several views of the drawings.

DETAILED DESCRIPTION

Example embodiments will now be described more fully with reference to the accompanying drawings.

Figure 1:
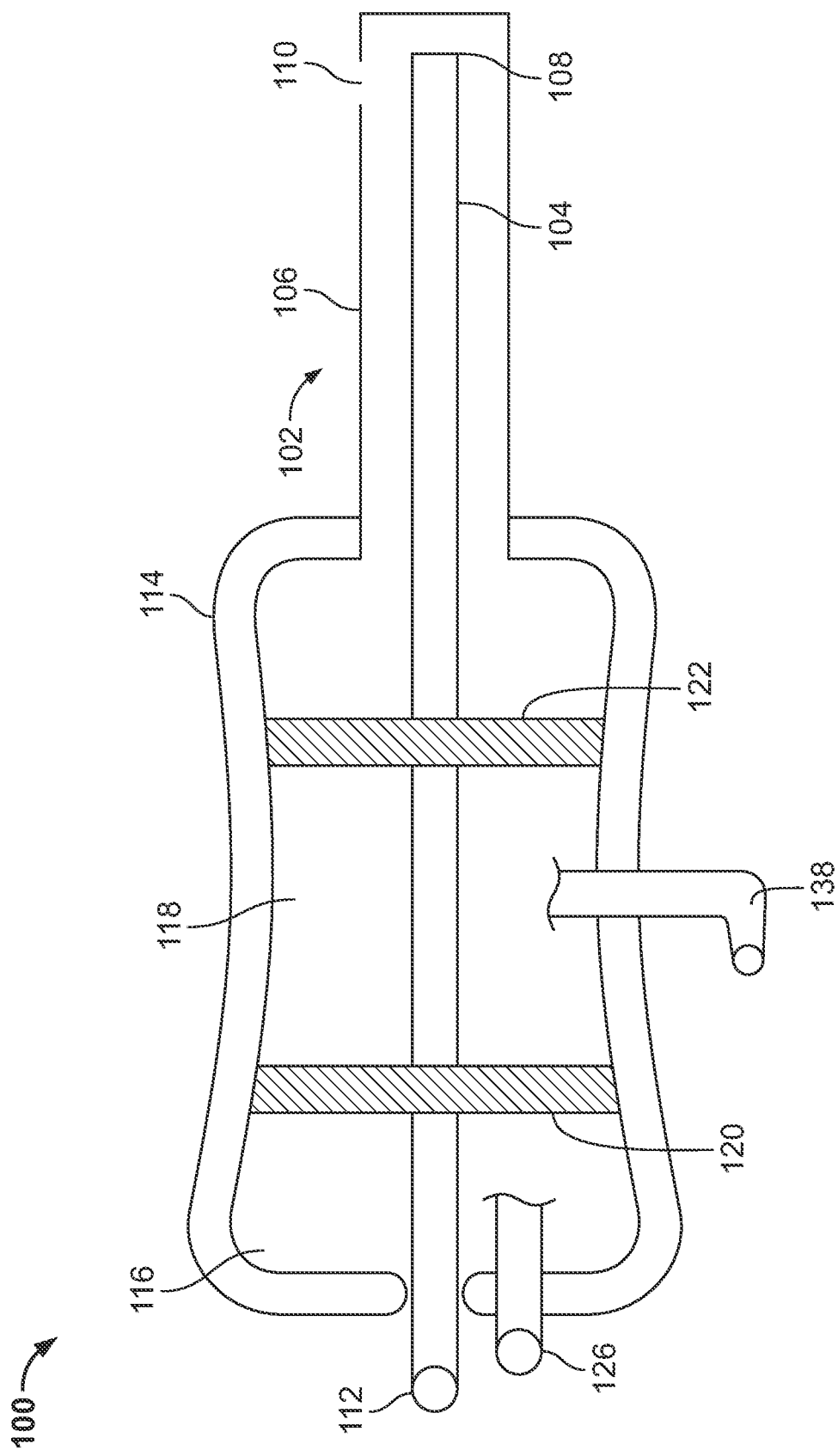
FIG. 1 is a view of a vitrectomy cutter of the present invention.

A surgical cutting apparatus, or vitrectomy cutter, according to one example embodiment of the present disclosure is illustrated in FIG. 1 and indicated generally by reference number 100. The vitrectomy cutter 100 includes a guillotine-type cutting assembly 102 for removing the vitreous from an eye during ophthalmic surgery. The cutting assembly 102 includes inner cutter cannula 104 which is configured to rapidly reciprocate or translate within an outer cutter cannula 106. The inner cutter cannula 104 includes a cutting edge 108 at a distal end or tip of the inner cutter cannula 104 and is a hollow or tubular shape which defines a passageway for aspirating and removing the vitreous from the eye. The outer cutter cannula 106 includes an aperture or port 110 through which the vitreous is drawn into the surgical cutting apparatus. As the inner cutter cannula 104 reciprocates within the outer cutter cannula 106, the vitreous, suctioned through the aperture 110, is cut as the cutting edge 108 of the inner cutter cannula 104 slides by the aperture 108 of the outer cutter cannula 106. The vitreous is aspirated and removed through an aspiration port 112 coupled to the inner cutter cannula 104.

The vitrectomy cutter 100 also includes a housing 114 coupled to the cutting assembly 102. The housing 114 contains a drive chamber 116 and a spring chamber 118. The drive chamber 116 is adapted to receive a pulse of compressed air within the drive chamber to drive or translate the inner cutter cannula 104 towards a closed position, cutting the vitreous of an eye. The spring chamber 118 is filled with a fluid such as air and, when pressurized, functions as a spring to bias and/or return the inner cutter cannula 104 towards a retracted or open position. The drive chamber 116 is separated from the spring chamber 118 by a first diaphragm 120. The first diaphragm 120 is fixed to an inner surface of the housing 114 and is positioned between the drive chamber 116 and the spring chamber 118. In this way, the first diaphragm 120 interfaces with the drive chamber 116 and the spring chamber 118. The housing 114 also includes a second diaphragm 122 which is adhered to the inner surface of the housing 114. The spring chamber 118 is defined by the first diaphragm 120 and the second diaphragm 122. The second diaphragm 122, depending on the application, may also be a rigid wall that effectively does not deflect during use compared to first diaphragm 120.

The inner cutter cannula 104 passes through the first and second diaphragms 120, 122. Generally, the inner cutter cannula 104 is positioned through the center of the first and second diaphragms 120, 122. As shown in FIG. 1, the first and second diaphragms 120, 122 are generally perpendicular to the inner cutter cannula 104. In the exemplary embodiment, the inner cutter cannula 104 is adhered to the first diaphragm 120. In some embodiments, the second diaphragm 122 is also adhered to the inner cutter cannula 104. In all embodiments second diaphragm 122, whether adhered to inner cutter cannula 104 or not, there should be a seal or close tolerance between the second diaphragm 122 and the inner cutter cannula 104 to allow the spring chamber 118 to be pressurized. Of course, in some embodiments, a design accommodating leakage between the diaphragm and the inner cutter cannula may be desirable to allow greater freedom of movement of the inner cutter cannula; however, intentionally creating leakage may result in unwanted noise during use.

Figure 2:
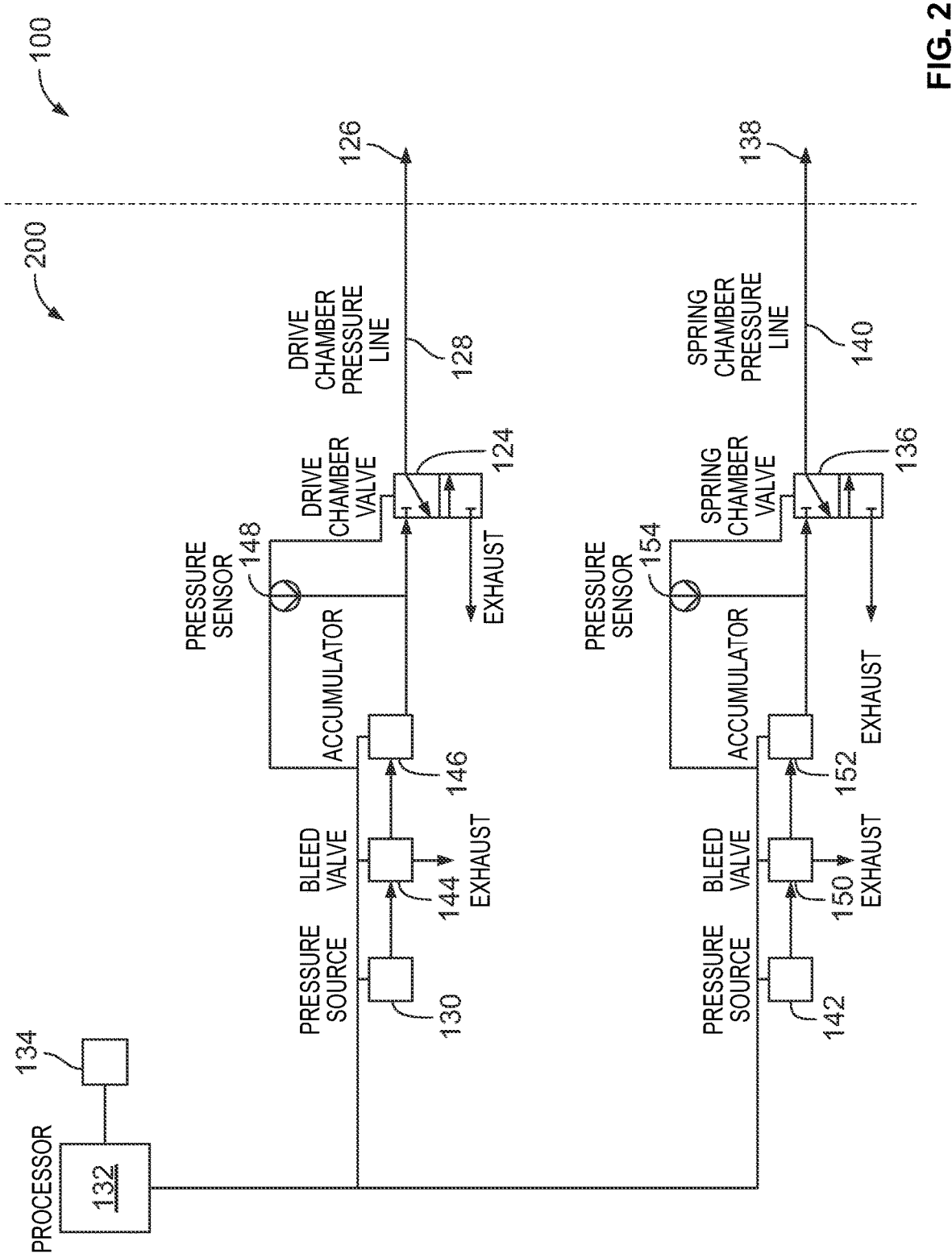
FIG. 2 is a schematic view of a control system coupled to the vitrectomy cutter of FIG. 1.

As shown in FIG. 2, the vitrectomy cutter 100 is coupled to a control system 200. The control system 200 includes a drive chamber valve 124 that is coupled to a port 126 of the drive chamber 116 of the vitrectomy cutter 100 through a drive chamber pressure line 128. The drive chamber valve 124 is adapted to supply compressed air to the drive chamber 116 and exhaust the compressed air from the drive chamber 116. In particular, a pressure source 130 is coupled to the drive chamber valve 124 and supplies a pulse of compressed air through the drive chamber pressure line 128 to the drive chamber 116 based on a desired cut rate. The processor 132 is configured to pulse the drive chamber valve 124 which causes the pulse of compressed air to enter the drive chamber 116 and the inner cutter cannula 104 to reciprocate at the desired cut rate. As compressed air is supplied to the drive chamber 116, the compressed air in the drive chamber 116 causes the first diaphragm 120 to move toward a distal end of the vitrectomy cutter 100 and compress the spring chamber 118. As the first diaphragm 120 moves, the inner cutter cannula 104 (which is adhered to the first diaphragm 120) translates within the outer cutter cannula 106 to a closed position, thereby cutting the vitreous of an eye.

When the pressure in the drive chamber 116 is reduced or released, the spring chamber 118 forces the inner cutter cannula 104 and the first diaphragm to return to the open position. The spring chamber 118 is pressurized, based on the desired cut rate, at a specified pressure to return and/or bias the inner cutter cannula 104. For example, when a high cut rate is desired (e.g., a high number of cutting strokes per minute), a greater spring force is required to return the inner cutter cannula 104 to the open position. This greater spring force ensures the inner cutter cannula 104 has fully returned to the open position before another pulse of compressed air is supplied to the drive chamber 116. Additionally, a pedal 134, such as a foot pedal, is coupled to the processor 132 to indicate the desired cut rate to the processor 132 based on the position of the pedal 134.

In some embodiments, the spring chamber 118 of the vitrectomy cutter 100 is sealed (e.g., is not coupled to a valve, a port 138 of the spring chamber 118 is closed, etc.) and the spring chamber is pressurized at a particular pressure such that the vitrectomy cutter 100 is operable over a range of cut rates. Alternatively, in the exemplary embodiment, the spring chamber 118 of the vitrectomy cutter 100 is not sealed and a spring chamber valve 136 is coupled to a port 138 of the spring chamber 118 through a spring chamber pressure line 140. The spring chamber valve 136 allows the pressure within the spring chamber 118 to be adjusted, for example, based on the desired cut rate. In particular, a pressure source 142 is coupled to the spring chamber valve 136 to supply pressurized air to the spring chamber 118 and exhaust the pressurized air from the spring chamber 118 through the opening and closing of the spring chamber valve 136 by the processor 132. In this way, the stiffness of the spring chamber 118 can be adjusted to allow the vitrectomy cutter 100 to operate over a broader range of cut rates.

In some embodiments, the processor 132 is configured to increase the air pressure within the spring chamber 118 via the spring chamber valve 136 when the desired cut rate is increased. In this manner, the stiffness of the spring chamber 118 is increased to allow the vitrectomy cutter 100 to operate at higher cut rates that require a greater spring force to return the inner cutter cannula 104 to the open position. Similarly, the processor 132 is also configured to decrease the air pressure within the spring chamber 118 via the spring chamber valve 136 when the desired cut rate is decreased. As the cut rate is decreased, a lower spring force is required to return the inner cutter cannula 104 to the open position such that the pressure within the spring chamber 118 may be reduced. In some embodiments, the processor 132 is configured to proportionally supply compressed air to the spring chamber 118 via the spring chamber valve 136 as the desired cut rate is increased and proportionally exhaust compressed air from the spring chamber 118 via the spring chamber valve 136 as the desired cut rate is decreased. In this way, the pressure within the spring chamber 118 is adjusted as the cut rate is adjusted, in a proportional manner. As can be appreciated, the drive chamber valve 124 and the spring chamber valve 136 are operated at different rates, even when both are operated based on the same desired cut rate. For example, the air supplied to the spring chamber 118 is not rhythmically pulsed with the air supplied to the drive chamber 116. Rather, for a given cut rate, compressed air from pressure source 130 is continuously pulsed into the drive chamber 116, but the pressure within the spring chamber 118 is not adjusted (e.g., no air is pulsed into the spring chamber 118).

Alternatively, rather than adjusting the pressure or stiffness of the air chamber 116 as the cut rate is adjusted, in some embodiments, the processor 132 is configured to increase the air pressure within the spring chamber 118 based on one or more thresholds. For example, as the cut rate is increased from a starting cut rate to a threshold cut rate (e.g., an upper threshold), the processor 132 does not adjust the air pressure within the spring chamber 118. Once the desired cut rate is above the threshold, the processor 132 operates the spring chamber valve 136 to supply compressed air from the pressure source 142 to the spring chamber 118. Similarly, in some embodiments, the processor 132 is configured to decrease the air pressure within the spring chamber when the desired cut rate is below a threshold cut rate (e.g., a lower threshold). In this way, once the desired cut rate, as indicated by pedal 134, is below the lower threshold, the processor 132 operates the spring chamber valve 136 to exhaust a specified amount of compressed air from the spring chamber 118 such that the pressure or stiffness of the spring chamber 118 is reduced.

As shown in FIG. 2, the processor 132 is further coupled to a bleed valve 144 to exhaust and/or relieve pressure, an accumulator 146, and a pressure sensor 148 for sensing the pressure of the air supplied to the drive chamber valve 124. The bleed valve 144, the accumulator 146, and the pressure sensor 148 are associated with the drive chamber 116. Additionally, the processor 132 is also coupled to a bleed valve 150, an accumulator 152, and a pressure sensor 154 which are associated with the spring chamber 118.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The invention claimed is:

1. A vitrectomy system comprising:
 a surgical cutting apparatus comprising:
  a cutting assembly including an outer cutter and an inner cutter;
  a housing coupled to the cutting assembly, the housing containing a drive chamber, a spring chamber, at least a first diaphragm, wherein the at least first diaphragm is adhered to the inner cutter and positioned between the drive chamber and the spring chamber;
  a drive chamber valve coupled to the drive chamber to supply compressed air to the drive chamber;
  a spring chamber valve coupled to the spring chamber to adjust air pressure within the spring chamber; and
 a processor operatively coupled to the surgical cutting apparatus and configured to:
  pulse the drive chamber valve based on a desired cut rate to translate the inner cutter at the desired cut rate; and
  set and maintain the air pressure in the spring chamber based on the desired cut rate for up to a threshold cut rate and adjust the air pressure within the spring chamber based on the desired cut rate only when the desired cut rate is above the threshold cut rate to adjust the stiffness of the spring chamber.

2. The vitrectomy system of claim 1, wherein the processor is further configured to increase and maintain the air pressure within the spring chamber via the spring chamber valve when the desired cut rate is increased above the threshold cut rate, and
 wherein the processor is further configured to decrease and maintain the air pressure within the spring chamber via the spring chamber valve when the desired cut rate is decreased below the threshold cut rate.

3. The vitrectomy system of claim 1, wherein the inner cutter is adhered to a second diaphragm.

4. The vitrectomy system of claim 1, further comprising a pedal coupled to the processor which indicates the desired cut rate to the processor based on the position of the pedal.

5. A vitrectomy system comprising:
 a surgical cutting apparatus comprising:
  a cutting assembly including an outer cutter cannula and an inner cutter cannula;
  a housing coupled to the cutting assembly including a drive chamber and a spring chamber;
  a first diaphragm coupled to the housing, wherein the first diaphragm is adhered to the inner cutter cannula and interfaces with the drive chamber and the spring chamber, wherein the spring chamber is defined by the first diaphragm and a wall of the housing, the wall substantially perpendicular to the inner cutter cannula;
  a drive chamber valve coupled to the drive chamber to supply compressed air to the drive chamber; and
  a spring chamber valve coupled to the spring chamber to adjust air pressure within the spring chamber;
 a processor operatively coupled to the surgical cutting apparatus and configured to:
 pulse the drive chamber valve based on a desired cut rate to translate the inner cutter at the desired cut rate; and
 set and maintain the air pressure in the spring chamber based on the desired cut rate for up to a threshold cut rate and adjust the air pressure within the spring chamber via the spring chamber valve based on the desired cut rate only when the desired cut rate is above the threshold cut rate.

6. The vitrectomy system of claim 5, wherein the processor is configured to supply the compressed air to the spring chamber when the desired cut rate is increased above the threshold cut rate.

7. The vitrectomy system of claim 5, wherein the processor is configured to decrease the air pressure within the spring chamber when the desired cut rate is decreased below the threshold cut rate.

8. The vitrectomy system of claim 5, further comprising a pedal coupled to the processor which indicates the desired cut rate to the processor based on the position of the pedal.

* * * * *